(12) United States Patent
Rowe et al.

(10) Patent No.: US 7,234,597 B2
(45) Date of Patent: Jun. 26, 2007

(54) APPARATUS AND METHOD FOR PACKAGING ELONGATE SURGICAL DEVICES

(75) Inventors: Howard V. Rowe, Mission Viejo, CA (US); Timothy C. Bell, Irvine, CA (US); Larry Bonzomet, Riverside, CA (US); William L. Patton, Rancho Mirage, CA (US)

(73) Assignee: Clean Cut Technologies, LLC, Fullerton, CA (US)

( * ) Notice: Subject to any disclaimer, the term of this patent is extended or adjusted under 35 U.S.C. 154(b) by 254 days.

(21) Appl. No.: 10/614,546

(22) Filed: Jul. 3, 2003

(65) Prior Publication Data

US 2004/0055919 A1    Mar. 25, 2004

Related U.S. Application Data

(60) Provisional application No. 60/408,085, filed on Sep. 3, 2002.

(51) Int. Cl.
*A61B 17/06* (2006.01)
(52) U.S. Cl. ..................... 206/438; 206/364
(58) Field of Classification Search ............... 206/63.5, 206/225, 227, 303, 364, 388, 438, 477, 481–483; 600/585, 434; D3/203.1
See application file for complete search history.

(56) References Cited

U.S. PATENT DOCUMENTS

| | | | |
|---|---|---|---|
| 1,323,039 A | 11/1919 | Frederick | |
| 3,312,579 A * | 4/1967 | Heifetz | 156/305 |
| 3,802,987 A | 4/1974 | Noll | |
| 4,332,322 A * | 6/1982 | Jaeschke et al. | 206/364 |
| 4,607,746 A | 8/1986 | Stinnette | |
| 5,125,416 A | 6/1992 | Phillips | |
| 5,131,537 A * | 7/1992 | Gonzalez | 206/364 |
| 5,247,942 A * | 9/1993 | Prather et al. | 600/585 |
| 5,344,011 A | 9/1994 | DiBernardo et al. | |
| 5,466,322 A | 11/1995 | Munsch | |
| 5,497,601 A * | 3/1996 | Gonzalez | 53/449 |
| 5,525,178 A | 6/1996 | Roggenbuck | |
| 5,591,292 A | 1/1997 | Blomqvist | |
| 5,840,151 A | 11/1998 | Munsch | |
| 5,848,691 A | 12/1998 | Morris et al. | |
| 5,944,701 A | 8/1999 | Dubrul | |
| 5,958,167 A | 9/1999 | Van Driel et al. | |
| 6,047,825 A | 4/2000 | Samuels | |
| 6,053,313 A | 4/2000 | Farrell et al. | |
| 6,375,006 B1 | 4/2002 | Samuels | |
| 2001/0000263 A1 | 4/2001 | Baumgartner | |

\* cited by examiner

*Primary Examiner*—David T. Fidei
(74) *Attorney, Agent, or Firm*—Myers Dawes Andras & Sherman LLP; Vic Lin

(57) ABSTRACT

A package for an elongate surgical device, such as a catheter, includes an elongate tube formed into a coil configuration with a first coil portion disposed adjacent to a second coil portion. A thermal weld bonds the coil portions in a fixed relationship and with a strength sufficient to prevent peeling the first coil portion from the second coil portion. The surgical device can then be loaded into the tube, pouched and sterilized for ultimate distribution. In an associated method, the tube is coiled on a turntable and moved relative to heating stations where the thermal bonds can be formed.

16 Claims, 5 Drawing Sheets

APPARATUS AND METHOD FOR PACKAGING ELONGATE SURGICAL DEVICES

PRIORITY CLAIM

This patent application claims the benefit of the priority date of U.S. Provisional Patent Application Ser. No. 60/408,085, filed on Sep. 3, 2002 and entitled GUIDEWIRE/CATHETER PACKAGING TUBE pursuant to 35 USC 119, the entire contents of this provisional patent application are hereby expressly incorporated by reference.

BACKGROUND OF THE INVENTION

The present invention relates generally to packages for surgical devices, and more specifically to packages including a tube for packaging elongate surgical devices such as catheters and guidewires.

DISCUSSION OF THE PRIOR ART AND RELATED INFORMATION

There are many surgical devices that are designed to navigate torturous conduits within the human body. Representative of these devices are catheters and guidewires that typically have diameters in a range of 1 French to 20 French and lengths in a range of 12 to 200 inches. These are flexible devices capable of being formed into smaller volumes to facilitate packaging and distribution of the products. One form of packaging that is particularly common includes a coiled tube having a lumen into which the surgical device can be loaded without kinking or distorting the device.

In the past, formation of this coiled tube package has been difficult as the coils have a natural tendency to separate. In an effort to maintain the coiled configuration of the tube, various mechanical clips have been formed to individually engage the coils and hold them in close proximity. By maintaining each of the coils in a fixed relationship with the clip, the coiled configuration of the tube can be loosely maintained.

After the coiled tube has been formed and the device has been loaded, the device and tube is enclosed in a pouch and sealed for sterilization and ultimate distribution of the product. The coiled tube is typically supplied to the manufacturer of the surgical device. The device has then been loaded into the coiled tube and a lid is sealed over the tube and thermoformed tray to provide a sterilizable and hermetically sealed chamber for the surgical device.

Unfortunately, the mechanical clips have not provided a satisfactory means for maintaining the coiled configuration of the tube. The clips have been formed with sharp edges and points, which have tended to puncture the pouch thereby compromising the sterility of the device. These clips have added significantly to the cost of the packaging, and have been both labor intensive and time consuming to apply. Furthermore, they have not provided a rigid structure for maintaining the coiled configuration of the tube. In addition, retention accessories such as injection molded cups, connectors, clips, thermal formed trays and the like have been used to facilitate mechanical retention of component and accessories for said device. The retention accessories are typically affixed by means of snap fit, gluing and chemical bonding.

SUMMARY OF THE INVENTION

In accordance with the present invention, these deficiencies of previous coiled packages have been overcome by providing a thermal bond between portions of the adjacent tube coils. The bond can be formed as a single, continuous spiral weld or as a plurality of spot welds. In either case, adjacent coils in the coiled stack, or profile, are bonded together in a fixed relationship, which greatly facilitates the remaining steps in the packaging process.

The tube can be coiled in many different configurations, each being stabilized with one or more of the thermal bonds. For example, the coil can be wound in a spiral configuration that can be formed in a single plane. In this configuration, the coils of the spiral have diameters that increase outwardly. In another embodiment, the coils are formed with a constant diameter so that the coil configuration forms a cylinder. In this configuration, the thermal bonds can also be formed between adjacent coils to maintain a cylindrical configuration. These two configurations can be used in a third combination for packaging more than one elongate device, each in a separate coiled tube. For example, a guidewire might be packaged in a first tube formed as a spiral in a first plane, while the catheter might be packaged in a second tube formed as a spiral in a second plane and stacked on top of the first tube. In this case, thermal bonds can be formed between the two tubes as well as between the coils of the tubes.

Thermal bonds can also be used to attach the coiled tubes to a backing card which acts as a labeling surface and a retention element and also to attach stand alone retention accessories to the tubes. Thus, the thermal bonds aid significantly in forming a rigid package that can ultimately be enclosed in a pouch without fear of compromising the integrity of the pouch.

In one aspect, the invention includes a package for an elongate surgical device where the package is formed with an elongate tube having walls defining a lumen between a first end and a second end of the tube. The tube is formed into a coiled configuration with a first coil portion disposed adjacent to a second coil portion. A thermal weld bonds the first coil portion to the second coil portion in a fixed relationship, and provides a strength sufficient to prevent peeling the first coil portion from the second coil portion.

Another aspect of the invention includes a method for packaging an elongate surgical device having an outside diameter. An elongate tube is provided having a tube wall with an inside diameter greater the outside diameter of the device. This tube is coiled to move a first tube portion into an adjacent relationship with a second tube portion. These two adjacent tube portions can then be thermally bonded so that the walls of the adjacent tube portions are maintained in a fixed relationship without occluding the tube. One or more of these bonds can be used to maintain the tube in a coiled configuration. A bridge can also be used to thermally bond the coils in the desired fixed relationship. A backing card formed of the same material as the tubing can be used to carry the coiled tube and otherwise facilitate components and accessories during the packaging process. The coils can be formed into a single layer with adjacent coils increasing outwardly in diameter. Alternatively, the coils can be formed with a constant diameter to form a stack of the coils. In either configuration, the coils can be formed from a single tube for packaging a single device, or multiple tubes for packaging multiple devices.

In a further aspect of the invention, a package is formed by providing an elongate tube having walls defining a lumen between a first end and a second end of the tube. The first end of the tube is attached to a fixture having at least one heating station and a turntable rotatable relative to the heating station. The turntable can then be rotated to form the tube into at least coil having adjacent coiled portions. By bonding the adjacent coiled portions at the heating (thermal transfer) station, the coiled configuration of the tube can be permanently maintained. On the turntable, the tube can be formed into multiple coils having a single layer or multiple coils formed as a stack with multiple layers. The adjacent coiled portions can be heated by directing heated air onto the coiled portions, by contacting the coiled portions with a heating element, by directing a laser beam onto the coiled portions and other thermal transfer methods. In all cases, the material of the coils becomes plasticized to form the thermal bonds.

DETAILED DESCRIPTION OF THE PREFERRED EMBODIMENTS AND BEST MODE OF THE INVENTION

Figure 1:
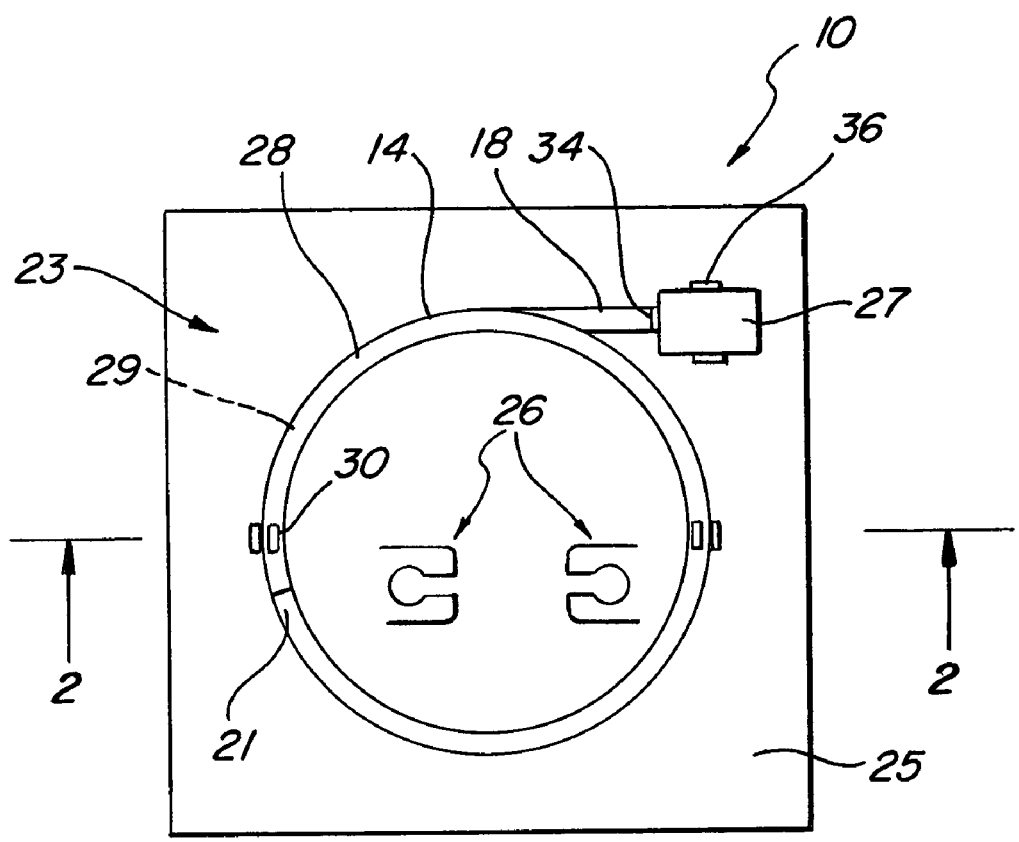
FIG. 1 is a top plan view of a medical device package of the present invention.
Figure 2:
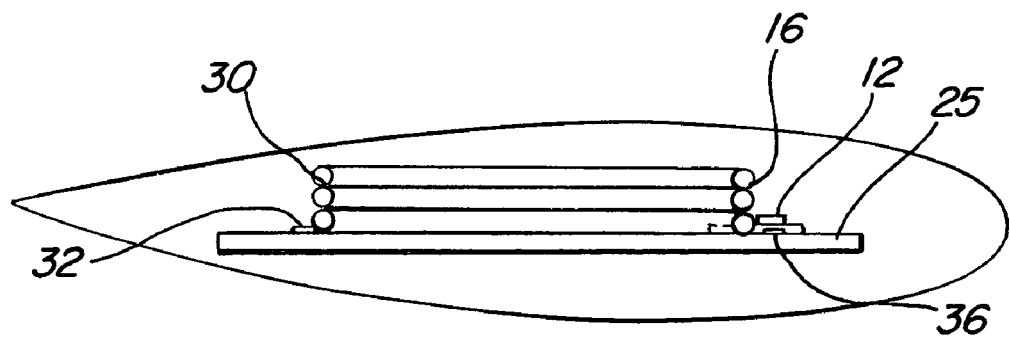
FIG. 2 is a cross section view taken along lines 2—2 of FIG. 1, with the addition of a guidewire/catheter and enclosing pouch.

A guidewire/catheter package is illustrated in FIGS. 1 and 2 and designated by the reference numeral 10. Although the package 10 is specifically adapted to retain, transport, distribute, and deliver a catheter or guidewire 12, it will be apparent that the package 10 can be adapted for use with any flexible elongate surgical instrument.

In the illustrated embodiment, the package 10 includes at least one tube 14 having a lumen 16 (best shown in FIG. 2) that extends between opposing ends 18 and 21. The tube 14 is formed as a coil assembly 23. In order to facilitate the attachment of clips, connectors, adapters or components commonly used for the retention and assembly of other surgical devices and peripheral components. The coil assembly 23 may be carried on a backing card 25 with component retention capabilities. For example, the backing card 25 may be provided with retaining mechanisms 26 configured to retain such components. For instance, the retaining mechanisms 26 may comprise tongue-and-groove portions cut out of the backing card 25 itself. As a further example, a retention accessory 27 may alternatively or additionally be coupled to end 18 and/or 21 of the tube 14 to facilitate the attachment of such components. It is to be expressly understood that a backing card 25 and a retention accessory 27 may be used independently of, or in combination with, each other.

In the coil assembly 23, tube portions 28 and 29 can be brought into an adjacent relationship. Thermal bonds 30 can then be created between these tube portions 28 and 29 to maintain the coiled configuration. Thermal bonds 32 can also be created between the coil assembly 23 and the backing card 25. Similarly, the retention accessory 27 can be attached to the end 18 and/or 21 of the tube 14 by a thermal bond 34, and attached to the backing 25 by an optional thermal bond 36.

As an example and not by way of limitation, thermal bonding can be formed using a process utilizing means of heating including but not limited to, heating elements, hot air, heaters, heating plates, laser or the combination thereof (herein referred to as "thermal bonds") where the material plasticizes and conjoins the surfaces of the tubing coils together. The process of thermally bonding the tubing together is applied to join singular or a plurality of tubes to form a coiled packaging, holding and dispensing tube ("packaging tube") that is not intended to be separated. The thermal bonds may be intermittent, continuous from tube to tube or may be formed by the application of a "bridge bond" where a separate piece of like material is thermally bonded to a side of the coiled tubing conjoining all coils together. Equipment used to manufacture the package 10 may utilize thermal/heating elements that can be in a singular processing configuration or in a multiple processing configuration allowing for higher production throughput and can be manually operated or automated to increase cycle time.

The manufacturer of the guidewire or catheter 12 may either manufacture the package or purchase the package from an outside vendor. In either case, the manufacturer will be responsible for loading the guidewire or catheter 12 into the coil assembly 23. Typically, one end of the guidewire or catheter 12 is inserted into the end 18 of the tube 14 and pushed through the lumen 16 of the tube 14 until the entire catheter 12 is substantially enclosed by the tube 14. The resulting subassembly including the backing card 25, coil assembly 23, retention accessory 27 (if any), and the catheter 12 can then be inserted into a pouch 31 and suitably sealed to facilitate sterilization, for example, by gamma ethylene oxide, e-beam, or other validated sterilization technique.

Figure 3:
FIG. 3 is a is a side elevation view of a catheter representative of any elongate surgical device.

The features and advantages of the present invention can be best understood with an appreciation of the nature of the guidewire or catheter 12, which is illustrated in FIG. 3. The elongate surgical device represented by the catheter 12 may have a diameter ranging in French sizes from 1 French to 20 French. This narrow diameter will usually be maintained along the body of the catheter and through a distal end 41. At a proximal end 42, the catheter may be provided, for example, with lures, connectors, stylets, mandrels, needles, tubing, or in the illustrated embodiment, a hub 43. The length of the guidewire or catheter 12 may be in a range of 12 to 200 inches. In order to provide for a package 10 of reduced size, it is desirable to bend the catheter 12 without kinking or in any other way degrading its structural performance.

Figure 4:
FIG. 4 is a side elevation view of a tube used in the package illustrated in FIG. 1.

A length of the tube 14 is illustrated in FIG. 4. In this case, the tube 14 has a cylindrical configuration, but it may also be tapered between the ends 18 and 21. Thus, the tube 14 may be extruded in a uniform or tapered cross section to accommodate various surgical device configurations, and provided with an overall length that typically exceeds that of the surgical device. Thus, the tube 14 may have a length in a range slightly greater than 12 and 200 inches, with the lumen 16 having a diameter of about 0.030 to 0.300 inches. Outer diameters of the tube 14 will typically range between 0.100 and 0.500 inches. A typical wall thickness of the tube 14 will be in a range between 0.010 and 0.100 inches. In certain preferred embodiments of the invention, the coil assembly 23 will have a diameter between 3 inches and 24 inches. This diameter, of course, will depend on the stacking tolerance of the coil assembly 23 and the wall thickness of the tube 14.

Figure 5:
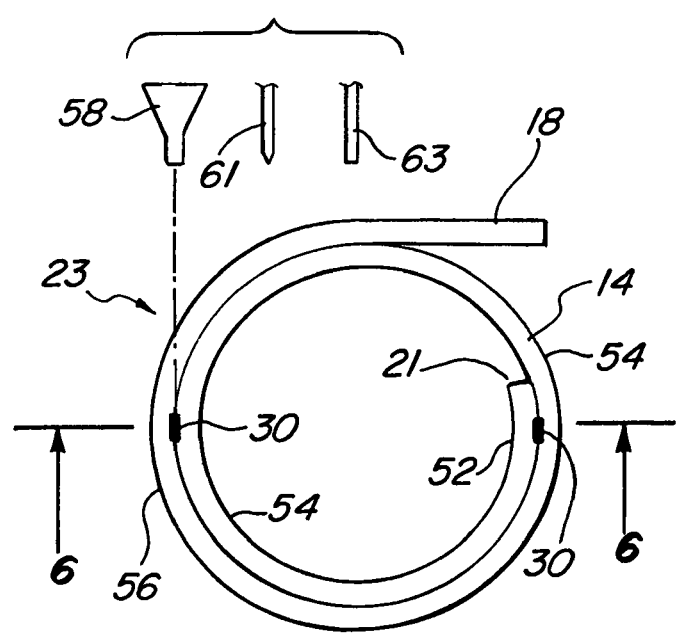
FIG. 5 is a top plan view illustrating formation of a thermal bond between adjacent coils of the tube.
Figure 6:
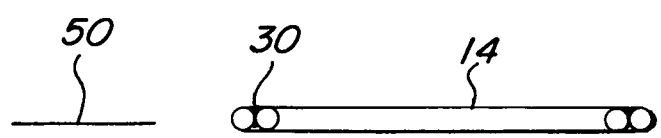
FIG. 6 is a cross section view taken along lines 6—6 of FIG. 5.

In the plan view of FIG. 5 and cross section view of FIG. 6, the coil assembly 23 is illustrated in a spiral configuration wherein the tube 14 is coiled in a single plane 50, as shown in FIG. 6. In this configuration, the tube 14 is provided with multiple coils 52, 54, and 56, which increase in diameter outwardly from the end 21 to the end 18. With this configuration, the thermal bonds 30 are formed between adjacent coils such as between the coils 52 and 54 and between the coils 54 and 56. These bonds 30 maintain the coils 52, 54, and 56 in a fixed relationship so that they cannot be separated or peeled.

The bonds 30 between the coils 52, 54 and 56, as well as the bonds 32, 34, and 36, can be formed with a variety of techniques as shown in FIG. 5. Hot air from a nozzle 58 can be directed at the interface between adjacent coils, for example. As an alternative, the thermal bonds can be formed using a heating element, which might include a heating probe 61 or heating plate, for example. As a further alternative, a laser 63 might be used to form the thermal bonds 30, 32, 34, and 36.

These heating devices 58, 61, and 63 are particularly advantageous when the structures to be bonded are formed of the same plastic material such as polyethylene, polypropylene, polyvinyl chloride, or other poly-related material. As the materials of the various elements are heated, they tend to plasticize, conjoining the surfaces of the elements in a fixed, non-peelable relationship. It is of particular importance with respect to the thermal bonds 30 that the adjacent walls of the tube 14 be bonded without occluding the lumen 16.

Figure 7:
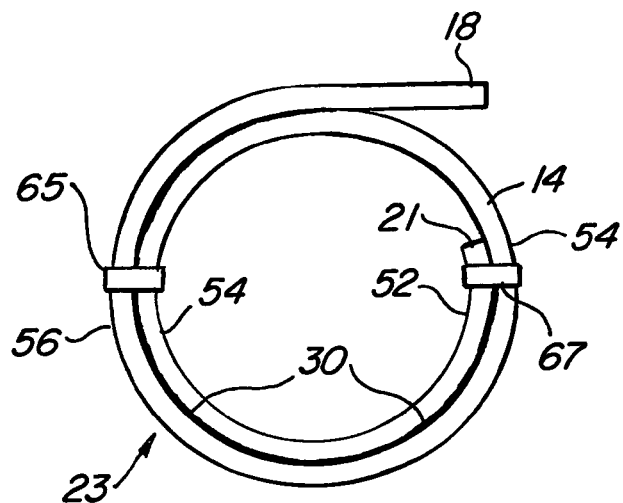
FIG. 7 is a top plan view illustrating use of bridges to form the rigid coil tube configuration.
Figure 8:
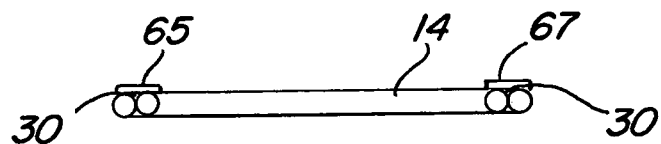
FIG. 8 is a cross section view taken along lines 8—8 of FIG. 7.
Figure 9:
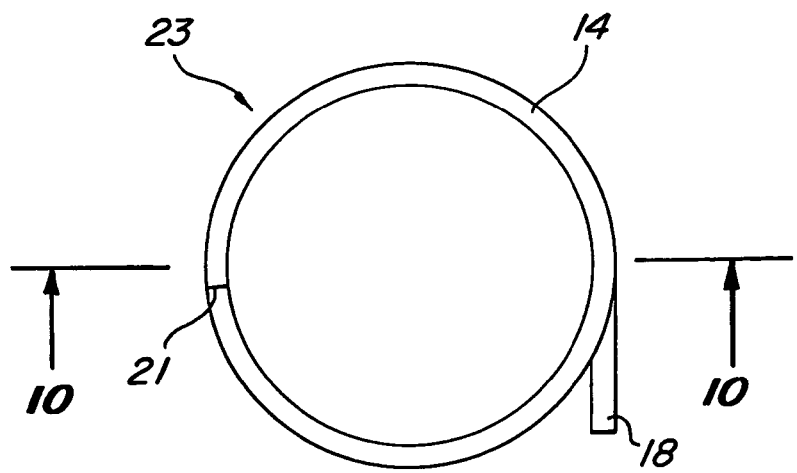
FIG. 9 is a top plan view of a further embodiment including stacks of tube coils.
Figure 10:
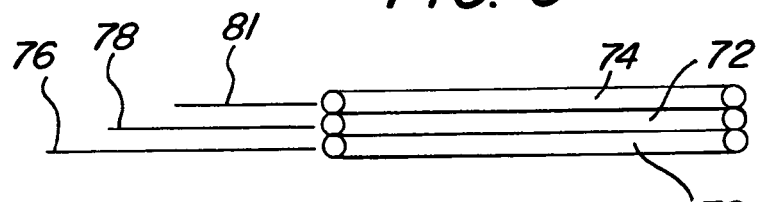
FIG. 10 is a cross section view taken along lines 10—10 of FIG. 9 illustrating multiple coils, each disposed in an associated plane.

The embodiment of FIGS. 7 and 8 is similar to that of FIGS. 5 and 6 in that the coils 52, 54, and 56 are spiraled in the single plane 50. In this case, however, the thermal bonds are not only formed directly between the coils 52, 54, and 56, but are also individually formed between each coil and a pair of bridges 65 and 67. The bridges 65, 67 in this case are merely pieces of plastic formed of a material common to the tube 14 and laid along a side of the coils 52, 54, and 56. One of thermal bonds 30 can be formed at the junction of each of the coils 52, 54, and 56 with the bridges 65 and 67. A further embodiment of a coil assembly 23 is illustrated in FIGS. 9 and 10. As shown in FIGS. 9 and 10, a tube 14 extends from one end 18 to an opposite end 21 to form stacked coils 70, 72, 74, each with an associated plane 76, 78, 81, respectively.

Figure 11:
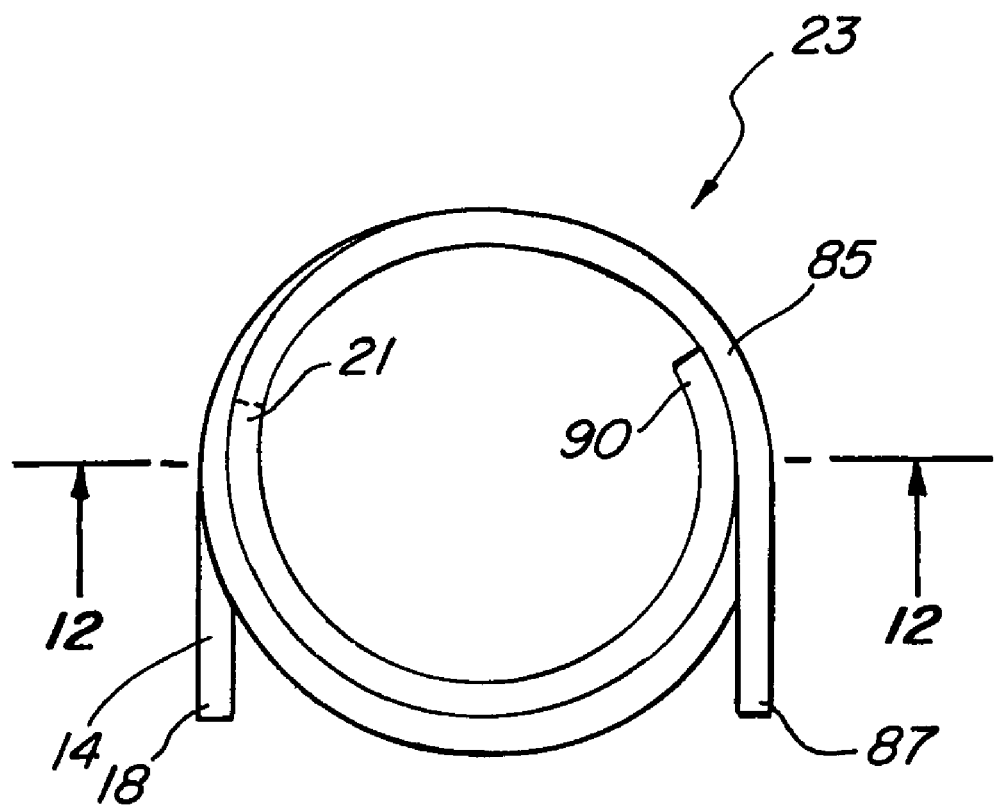
FIG. 11 is a top plan view of a coil configuration including multiple coil stacks of multiple tubes.
Figure 12:
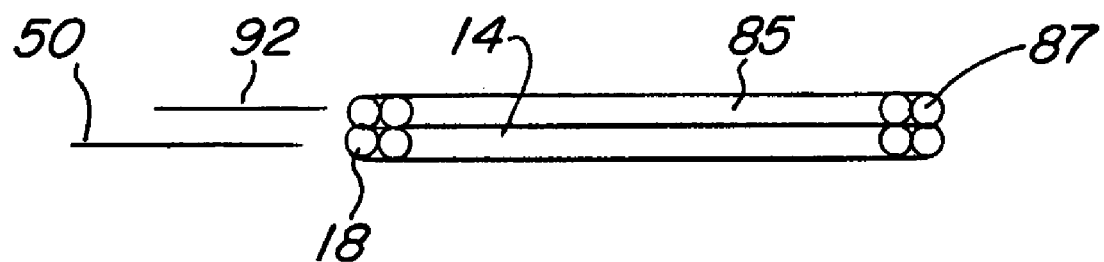
FIG. 12 is a cross section view taken along lines 12—12 of FIG. 11.

A further configuration of the coil assembly 23 is illustrated in the plan view of FIG. 11 and cross section view of FIG. 12. This assembly 23 is of particular advantage when more than one surgical device, such as a guidewire and a catheter, are to be packaged together. This is often the case when a particular guidewire is to be used with a particular catheter. In the illustrated embodiment, two separate package tubes are provided, each having a pair of ends. Thus, the tube 14, with its ends 18 and 21, is illustrated in FIG. 18 in a first spiral and single plane 50. In addition, a second tube 85, having ends 87 and 90, is illustrated in a second spiral and second plane 92. In the illustrated embodiment, the outer ends 18 and 87 of the tubes 14 and 85 respectively, are positioned on opposite sides of the coil assembly 23.

Figure 13:
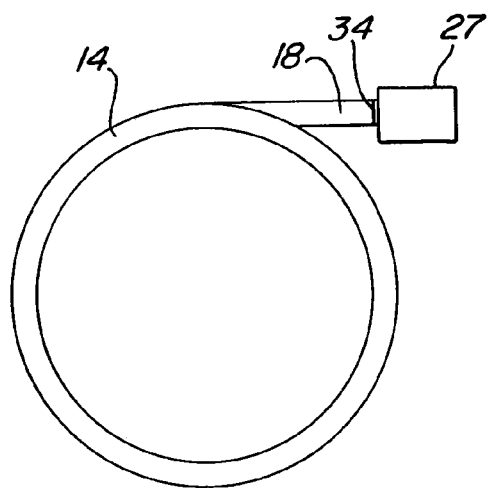
FIG. 13 is a top plan view illustrating a retention accessory thermally bonded to a coiled tube.

After the coil assembly 23 has been formed and appropriately bonded, the retention accessory 27 can be coupled to the end 18 and/or 21 of the tube 14 as illustrated in FIG. 13. As noted, the retention accessories 27 are individually designed and manufactured typically by die cutting, to accommodate various device components, such as the hub 43 (FIG. 3). The retention accessory may be coupled to the coil assembly 23 by strapping, snapping, gluing, mechanical bonding, or thermal bonding as previously discussed.

Figure 14:
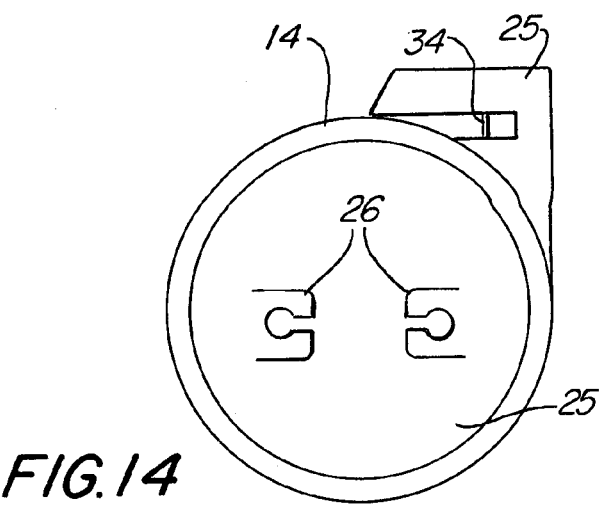
FIG. 14 is a top plan view illustrating the coiled tube thermally bonded to a backing card acting as a retention accessory and labeling surface.

Alternatively, in FIG. 14, retention capabilities may be provided in the backing 25 by forming, for example, retaining mechanisms 26. These retaining mechanisms 26 may be formed integrally the backing, for instance, by simply making cut-outs.

Figure 15:
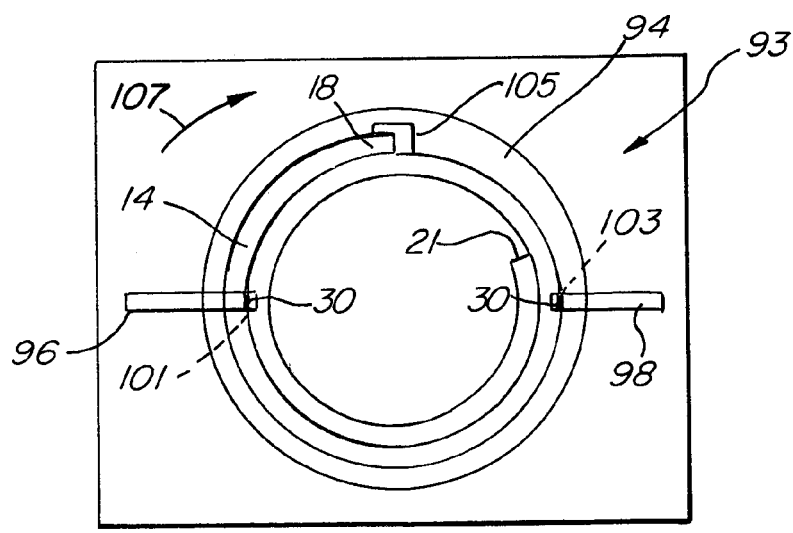
FIG. 15 is a top plan view of a fixture illustrating steps in the manufacture of the coiled tubing and associated thermal bonds.

A preferred fixture 93 for forming the coil assembly 23 with the thermal bonds 30 is illustrated in the top plan view of FIG. 15. In this case, the fixture 93 includes a turntable 94 that is rotatable relative to a pair of opposing heat stations 96 and 98. Heating elements, such as hot air nozzles 101 and 103, are provided in each of the heating stations 96 and 98, respectively. In operation, the end 18 of the tube 14 is initially positioned against a stop 105, and the turntable 94 may be rotated in the direction of arrow 107. After or concurrent to the coils of the tube establishing an adjacent relationship, the nozzles 101 and 103 can be activated to create individual thermal welds 30. This heating step may be accomplished with the turntable 94, either stationary or rotating. In a rotating mode, the nozzles 101 and 103 can be intermittently activated to create the spot welds 30 or can be continuously activated to create a single continuous bond between the adjacent coils of the tube 14. If the welds 30 are formed with the turntable 94 in a stationary mode, the nozzles 101 and 103 can be manually adjusted to the coil interface. Alternatively, if the welds 30 are formed with the turntable 94 in a rotation mode, they can be automatically adjusted to follow the spiral interface of the coils.

In the preferred embodiments, the tube 14, backing card 25 and retaining accessory 27 are all composed of a common material in order to enable the thermal bonding as discussed above. As an example and not by way of limitation, the common material may comprise polyethylene.

Notwithstanding the forgoing detailed description of preferred embodiments, it will be apparent that many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different elements.

Also, the words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what incorporates the essential idea of the invention.

The invention claimed is:

1. A package for an elongate surgical device, comprising:
   an elongate tube having walls defining a lumen between a first end and a second end of the tube;
   the tube being formed into a coiled configuration with a first coiled portion disposed adjacent to a second coiled portion, the first coiled portion being composed of a plastic material, the second coiled portion being composed of the plastic material; and
   a curved thermal weld bonding the first coiled portion to the second coiled portion in a fixed, non-peelable relationship without additional adhesive materials.

2. The package recited in claim 1 wherein the thermal weld is continuous.

3. The package recited in claim 2 wherein:
   the tube is formed into a stack of coils; and
   the weld comprising a single continuous weld retaining the coils in a fixed relationship.

4. The package recited in claim 2 further comprising:
   a backing card carrying the tube in the coiled configuration.

5. The package recited in claim 4 further comprising:
   a pouch forming with the backing card a sterilizable, hermetically sealed, enclosure for the coiled tube.

6. The package recited in claim 4 wherein the backing card is composed of the plastic material.

7. The package recited in claim 1 further comprising:
   a retaining accessory coupled to the first end of the elongate tube.

8. The package recited in claim 7, wherein the retaining accessory is composed of the plastic material.

9. A package for an elongate surgical device, comprising:
   an elongate tube having walls defining a lumen between a first end and a second end of the tube;
   the tube being formed into a coiled configuration with a first coiled portion disposed adjacent to a second coiled portion, the first coiled portion and the second coiled portion being composed of a common material; and
   a curved thermal weld bonding the first coiled portion to the second coiled portion in a fixed, non-peelable relationship.

10. The package recited in claim 9, wherein the thermal weld comprises a separate bridge bond thermally bonded to the first coiled portion and the second coiled portion.

11. The package recited in claim 9, wherein the tube and the separate bridge bond are composed of the common material.

12. The package recited in claim 9, wherein the first coiled portion and the second coiled portion are disposed along a common plane.

13. The package recited in claim 9, wherein the thermal weld is continuous.

14. The package recited in claim 9, wherein the thermal weld is intermittent.

15. A package for elongate surgical devices, comprising:
    a first elongate tube having walls defining a first lumen between a first end and a second end of the first tube;
    the first tube being formed into a first coiled configuration with a first coiled portion disposed adjacent to a second coiled portion, the first coiled portion and the second coiled portion being composed of a common material;
    a first curved thermal weld bonding the first coiled portion to the second coiled portion in a first fixed, non-peelable relationship;
    a second elongate tube having walls defining a second lumen between a third end and a fourth end of the second tube;
    the second tube being formed into a second coiled configuration with a third coiled portion disposed adjacent to a fourth coiled portion, the third coiled portion and the fourth coiled portion being composed of the common material; and
    a second curved thermal weld bonding the third coiled portion to the fourth coiled portion in a second fixed, non-peelable relationship.

16. The package recited in claim 15, wherein:
    first coiled portion and the second coiled portion are disposed along a first plane; and
    third coiled portion and the fourth coiled portion are disposed along a second plane above the first plane.

* * * * *